United States Patent [19]
Li et al.

[11] Patent Number: 5,558,636
[45] Date of Patent: Sep. 24, 1996

[54] METHOD OF EFFECTING EMBRYO TRANSPLANT

[75] Inventors: Jiewen Li, Columbia; August Rieke, Bland; Billy N. Day, Auxvasse; Randall S. Prather, Rocheport, all of Mo.

[73] Assignee: Curators of the University of Missouri, Columbia, Mo.

[21] Appl. No.: 438,174

[22] Filed: May 9, 1995

[51] Int. Cl.⁶ ................................... A61M 31/00
[52] U.S. Cl. ........................ 604/49; 604/55; 604/171; 600/34
[58] Field of Search .................. 128/898; 606/126; 600/33–35; 604/49, 906, 28, 53, 54, 55, 93, 181, 73, 171

[56] References Cited

U.S. PATENT DOCUMENTS

| | | | |
|---|---|---|---|
| 4,453,936 | 6/1984 | Cassou | 604/263 |
| 4,642,094 | 2/1987 | North, Jr. et al. | 604/55 |
| 4,832,681 | 5/1989 | Lenck | 600/63 |
| 4,865,589 | 9/1989 | Simmet et al. | 604/171 |
| 5,147,315 | 9/1992 | Weber | 604/164 |
| 5,472,419 | 12/1995 | Bacich | 604/55 |

FOREIGN PATENT DOCUMENTS

6-154254  6/1994  Japan ...................... 600/34

OTHER PUBLICATIONS

C. Polge, B. N. Day, "Pregnancy Following Non–surgical Egg Transfer in Pigs", Apr. 15, 1968, published in *The Veterinary Record*.

M. M. Sims and N. L. First, "Nonsurgical Embryo Transfer in Swine", 1987 p. 386, published in the *Journal of Animal Science*, vol. 65, Supplement 1.

W. Hazeleger, P. Jenneskens and B. Kemp, Non–surgical Transfer of Porcine Blastocyst, Jan., 1995, p. 232, published in the *Theriogenology, an International Journal of Animal Reproduction*, vol. 43, No. 1.

"Reproduction Resources Artificial Breeding Equipment and Veterinary Supplies", no date, pp. 1A, 1B, 1–17, 17A (admitted prior art).

H.–D. Reichenbach, J. Modl, G. Brem, "Piglets Born After Transcervical Transfer of Embryos into Recipient Gilts", Veterinary Record (1993) 4 pages.

J. M. Galvin, D. B. Killian and A. N. V. Stewart, "A Procedure for Successful Nonsurgical Embryo Transfer in Swine", dated 1994, pp. 1280–1289.

*Primary Examiner*—Randall L. Green
*Assistant Examiner*—V. Alexander
*Attorney, Agent, or Firm*—Senniger, Powers, Leavitt & Roedel

[57] ABSTRACT

This invention is directed to a method of effecting the non-surgical transplant of embryos into the uterus of an animal. The method involves the use of a long tubular gripping instrument having an open forward end and an external gripping formation generally adjacent its forward end. A probe with a long tubular body having an open forward end extends axially inside the gripping instrument. A probing member projects in a generally non-axial direction from the probe body generally adjacent its forward end. The method comprises the steps of inserting the gripping instrument, forward end first, into a cervix of the uterus, and establishing a grip between the walls of the cervix and the external gripping formation on the gripping instrument. While maintaining said grip, the gripping instrument is pulled in a rearward direction to straighten the cervix. At the same time the the probe is pushed in a forward direction to advance the probing member through the cervix to a position generally adjacent a body of the uterus. An embryo carrier is then placed inside the probe body and moved to an embryo release position for release of embryos from the carrier into the uterus.

19 Claims, 7 Drawing Sheets

FIG. 1

METHOD OF EFFECTING EMBRYO TRANSPLANT

SUMMARY OF THE INVENTION

This invention relates generally to the nonsurgical transfer of embryos into animals, particularly pigs, although it is contemplated that this invention may be applied to other animals (e.g., certain breeds of cattle).

The nonsurgical transfer of embryos from a female donor animal to a female recipient animal has been employed for many years in the beef and dairy cattle industry to achieve the genetic improvement of breeds. However, in the porcine industry, attempts at nonsurgical embryo transfer have met with only limited success. This is due in large part to physiology. The cervical structure of a female pig is such that it is a barrier to nonsurgical methods of transfer.

One attempt at a non-surgical embryo transfer is described by J. M. Galvin et al. in "Theriogenology" 41:127917.8 –1289, 1289, 1994. The described procedure involves inserting a tubular instrument (spirette) into the cervix of a recipient pig, and then forcing 10–12 milliliters of liquid medium containing embryos into and through the instrument, the objective being to deposit the embryos in the uterus. However, this procedure has several serious drawbacks. First, there is no way to determine whether the instrument has been inserted far enough into the cervix so that its forward end is adjacent the body of the uterus. As a result, in instances where the forward end of the instrument remains lodged within the cervix, the embryos may never reach the uterus. Also, if the instrument is inserted too far, the uterus or surrounding tissue may be damaged. Another disadvantage of this procedure is that the relatively large quantity of liquid introduced into the cervix and uterus tends to make the uterine environment unsuitable for growth of the embryos.

There is a need, therefore, for an improved method of effecting the nonsurgical transfer of embryos into recipient animals, particularly those having a cervix of the type which is difficult to penetrate, such as pigs. This invention is directed to such a method.

Among the several objects and features of the present invention are the provision of an improved method of transferring embryos into a recipient animal; the provision of such a method which ensures that the embryos being transferred are properly placed in the uterus of the recipient animal, even though the cervix of the animal has an anatomical design which is difficult to penetrate; the provision of such an improved method which minimizes the risk of contamination, trauma and injury to the animal during the transfer procedure; the provision of such a method which effects transfer of the embryos with only a minimal amount of liquid medium so as not to disturb the natural environment of the uterus of the recipient animal; the provision of such a method which is easy to use and which effects the transfer very quickly and efficiently; the provision of such a method which is sanitary; the provision of such a method which results in an increased rate of pregnancy compared to prior procedures, and which results in litters of larger size; and the provision of such a method which is relatively inexpensive to carry out.

In general, this invention involves a method of effecting the non-surgical transplant of embryos into the uterus of an animal. The method involves the use of a long tubular gripping instrument having an open forward end and an external gripping formation generally adjacent its forward end, and a probe extending axially inside the tubular gripping instrument. The probe has a long tubular body with an open forward end and a probing member projecting in a generally non-axial direction from the probe body generally adjacent its forward end. The method comprises the steps of (1) inserting the gripping instrument, forward end first, into a cervix of the uterus of said animal, (2) establishing a grip between walls of the cervix and the external gripping formation on the gripping instrument, (3) while maintaining said grip, pulling the gripping instrument in a rearward direction to straighten the cervix and simultaneously pushing the probe in a forward direction to advance the probing member beyond the forward end of the gripping instrument and through the cervix to a position in the body of the uterus, and (4) placing an embryo carrier inside the probe body and moving the carrier forwardly thorugh the probe body out the open forward end of the probe body to an embryo release position for release of embryos from the carrier into the uterus.

In another aspect, the method comprises the steps of inserting a long tubular gripping instrument forwardly into the cervix to obtain a grip on the walls of the cervix, pulling the gripping instrument rearwardly to tension the cervix, and while pulling the gripping instrument rearwardly, inserting a long tubular probe into and through the gripping instrument to a point where a forward end of the probe is generally adjacent the body of the uterus. The method also involves inserting an embryo carrier into the probe and moving it forwardly through the forward end of the probe to an embryo release position in the uterus, and releasing embryos from the embryo carrier into the uterus.

Other objects and features will be in part apparent and in part pointed out hereinafter.

BRIEF DESCRIPTION OF THE DRAWINGS

Corresponding parts are designated by corresponding numerals throughout the several views of the drawings.

DESCRIPTION OF THE PREFERRED EMBODIMENT

Figure 1:
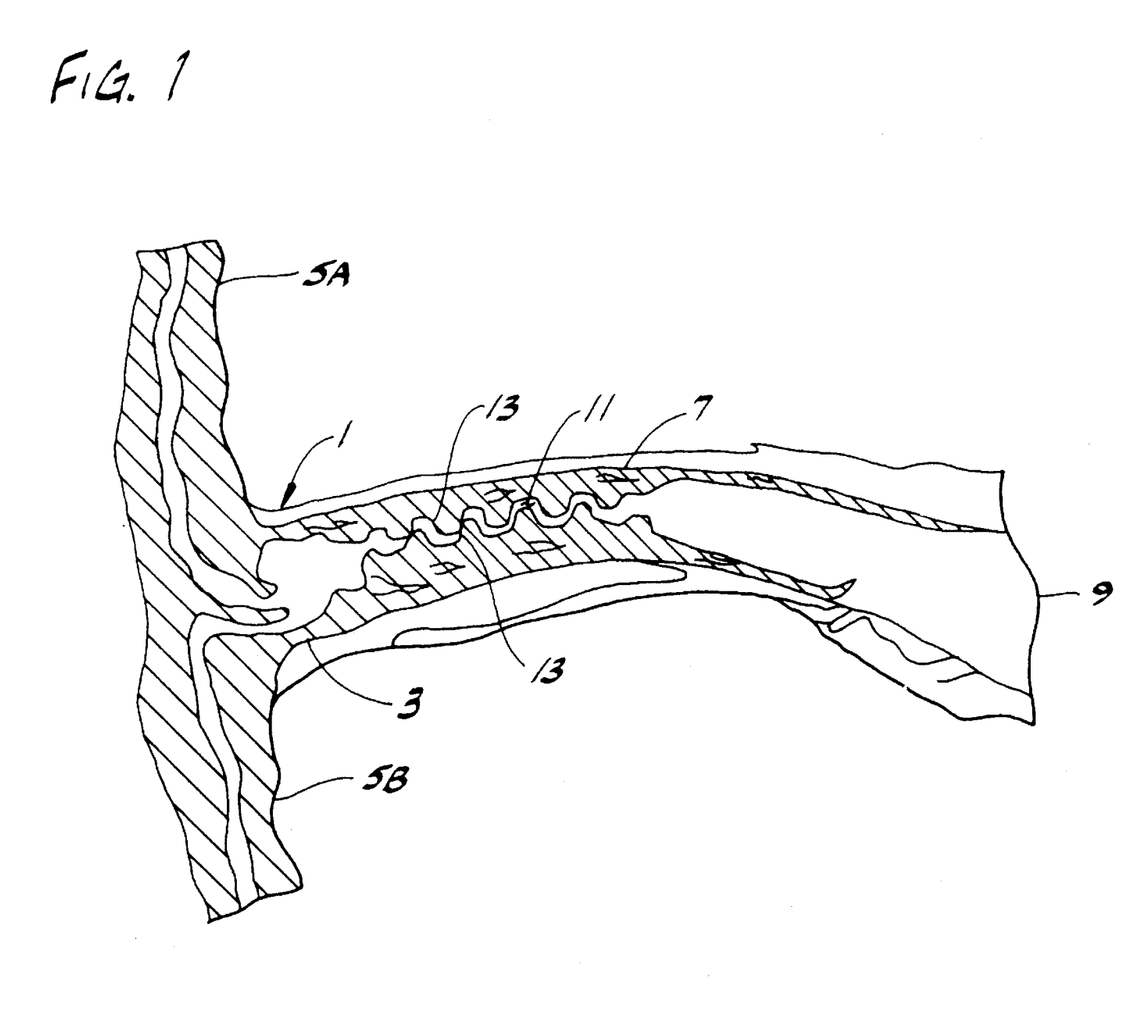
FIG. 1 is a schematic illustration of the uterus of a pig.

The drawings illustrate a system of this invention for effecting the nonsurgical transplant (transfer) of embryos into the uterus of an animal. This system is particularly applicable to pigs, but it will be understood that it may also be used to carry out nonsurgical embryo transfers in other animals. For purposes of illustration, FIG. 1 shows the anatomical configuration of the uterus of a pig. The uterus (which is generally designated 1) comprises a uterus body 3, a pair of horns 5A, 5B extending from the body, and a cervix 7 connecting the vagina 9 of the pig to the body 3 of the uterus. The inside walls defining the cervical canal 11 of the cervix are convoluted and lined with rounded prominences 13, some of which dovetail to occlude the canal. It is this anatomy which has hindered prior attempts to effect the non-surgical transfer of embryos.

Figure 2:
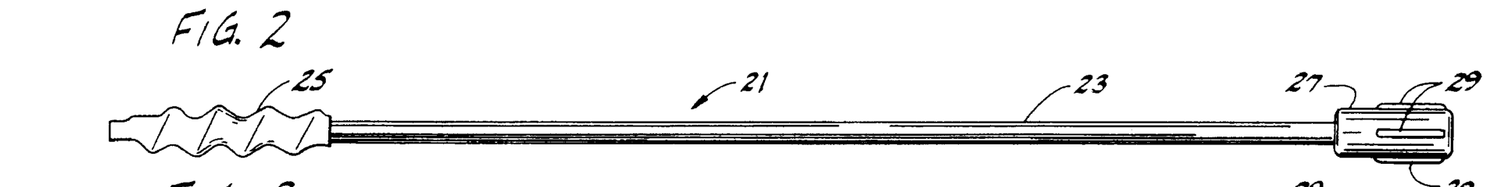
FIG. 2 is an elevation of a gripping instrument of the system of this invention.

The system of this invention includes five parts, the first of which is shown in FIG. 2. It comprises a gripping instrument, generally designated 21, having a long tubular body 23, an external gripping formation in the form of a screw (spiral) head 25 at the forward end of the body 23, and a handle 27 at the rearward end of the body formed with a series of ribs 29 to facilitate grasping and turning the instrument on its longitudinal axis. Both the screw head 25 and the handle 27 have bores in axial alignment with the bore through the body to provide a continuous passage 35 through the entire assembly from the rearward end of the handle to the tip of the screw head. The body 23, head 25 and handle 27 of the instrument 21 can be molded plastic parts, with the head being of a soft flexible material so as not to injure the animal when the instrument is inserted, head first, into the uterus, as will be described later. A suitable instrument of this type is commercially available from Swine Genetics International located in Cambridge, Iowa.

Figures 3, 4:
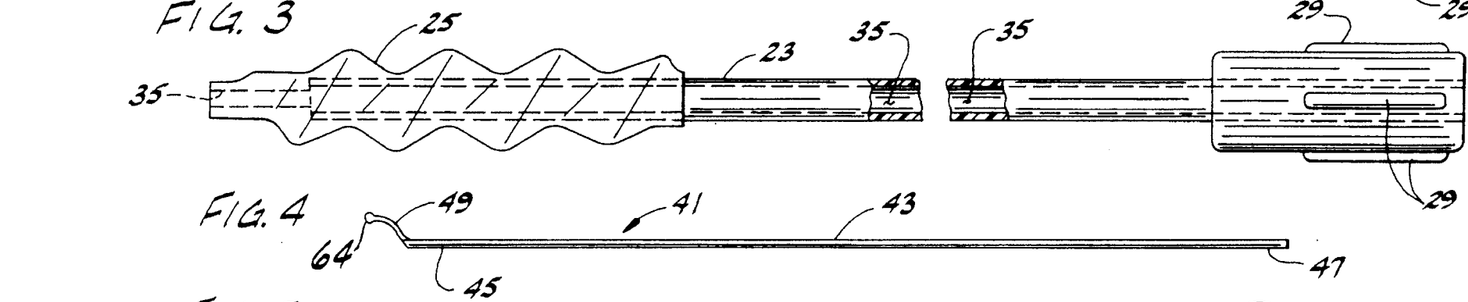
FIG. 3 is an enlarged view of front and rear end portions of the instrument of FIG. 2.
FIG. 4 is an elevation of a probe of the system.
Figure 5:
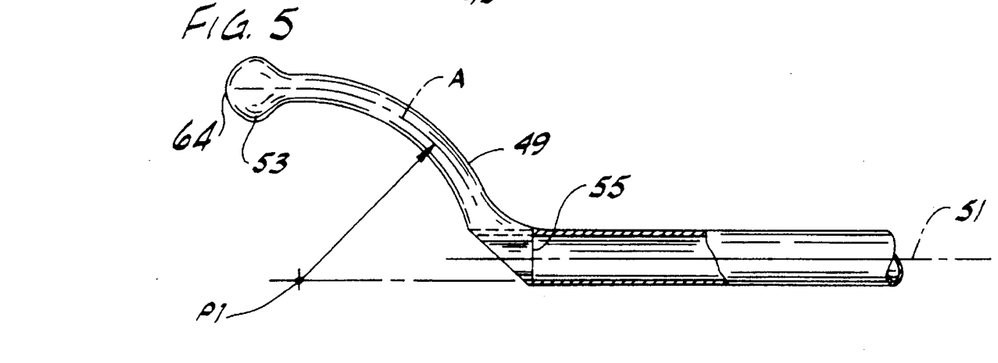
FIG. 5 is an enlarged view of a front end portion of the probe of FIG. 4.
Figure 6:
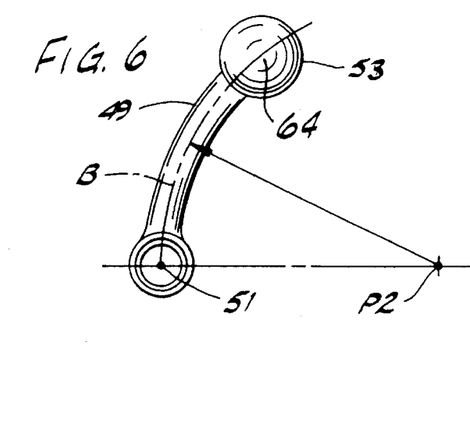
FIG. 6 is a left end view of FIG. 5.

The second part, shown in FIG. 4, comprises a probe generally indicated at 41 having a long tubular 43 body with open forward and rearward ends indicated at 45 and 47, respectively, and a probing member comprising a finger-like member 49 (or, more simply, a finger) projecting in an no-axial direction from the probe body generally adjacent its forward end. More specifically, as illustrated in FIGS. 5 and 6, the finger 49 arcs laterally outwardly and forwardly from the forward end of the probe body, the arc A shown in FIG. 5 being centered on a point P1 generally in-line with the probe body, and the arc B shown in FIG. 6 being centered on a point generally in-line with the central longitudinal axis 51 of the probe body. The finger has a blunt and enlarged forward end indicated at 53. The probe body 43 and finger 49 are preferably formed as a single piece of metal, such as stainless steel. The probe body may be formed from 12-gauge hypodermic stainless steel tubing having an outside diameter of 0.109 in. and an inside diameter of 0.085 in. By way of example, arc A may have a radius of about 0.43 in. and arc B may have a radius of about 0.5 in. For reasons which will become apparent hereinafter, the forward end 45 of the probe body is formed with an internal annular shoulder 55 forming an abutment (the inside diameter of the probe body rearward of this shoulder or abutment may be 0.109 in., for example, and the inside diameter of the probe body forward of this abutment may be 0.075 in., for example).

The probe 41 is sized to be slidably inserted, rearward end first, into the forward (head) end of the gripping instrument 21. It also has a length considerably longer than the gripping instrument so that, when fully inserted into the instrument, the rearward end 47 of the probe projects endwise beyond the rearward end of the instrument. By way of example, the gripping instrument 21 may have an overall length of 17.8 in., and the probe 41 may have an overall length of about 25.6 in. Thus, the rearwardly projecting end of the probe serves as a handle by which the probe may be grasped to manipulate the probe to rotate it and to move it forward and rearward relative to the gripping instrument from a fully retracted position in which the probing finger 49 is retracted inside the soft flexible head 25 of the instrument, and an extended position in which the probing finger is forward of the head 25 for probing through the cervix, as will be described later.

Figure 7:
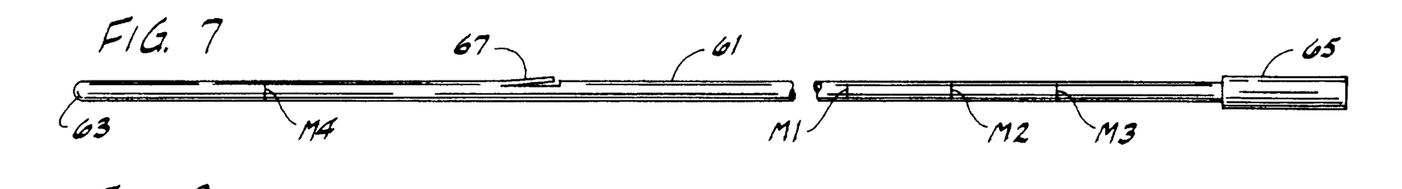
FIG. 7 is an elevation of a testing bar of the system.

The third part of the system is shown in FIG. 7 as comprising a long slender testing or detecting bar 61, preferably of round stainless steel bar stock having a rounded and polished forward end 63 (left end as viewed in FIG. 7). The bar is sized to be slidably inserted, forward end first, into the rearward end 47 of the probe body 43, and to be pushed forward so the forward end of the bar extends beyond the forward end 45 of the probe body 43 and beyond the tip 64 of the probing finger 49. The bar 61 is longer than the probe body so that when fully inserted into the probe body, the bar extends rearwardly from the probe body so that it may be grasped to move the bar back and forth relative to the probe body. By way of example, the bar 61 may have a diameter of 0.0625 in. and a length of 28 in. The rearward end 65 of the bar (e.g., the rearwardmost 1.0 in. of the bar) is enlarged to form a pusher. This pusher, the function of which will become apparent later, has a diameter (e.g., 0.083 in.) only slightly less than the inside diameter of the probe body 43. To facilitate proper use of the bar 61, it is marked as indicated at M1 with a first score line or the like to indicate visually when the forward end of the bar is coterminal with the forward end 45 of the probe body 43, and as indicated at M2 and M3 with second and third score lines or the like to indicate visually when the forward end of the bar projects predetermined distances (e.g., 1 in. and 2 in.) beyond the forward end of the probe body.

Figure 8:
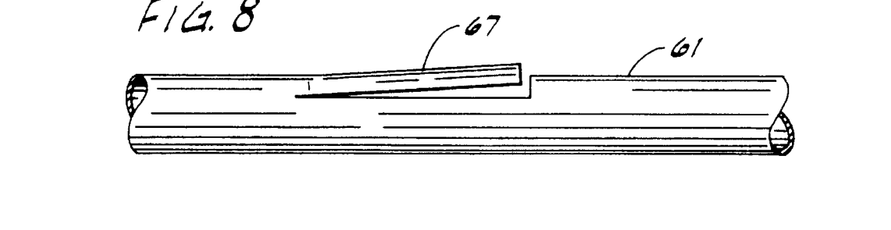
FIG. 8 is an enlarged view of a part of the testing bar of FIG. 7.

The testing bar 61 is formed to have a flexibly resilient tongue 67 spaced rearwardly (e.g., about 3.0 in.) from the forward end 63 of the bar. This tongue 67 is biased toward the position shown in FIG. 8 so that its rearward (free) end projects laterally outwardly from the bar. The purpose of this tongue will also become apparent later.

Figures 9, 10, 11:
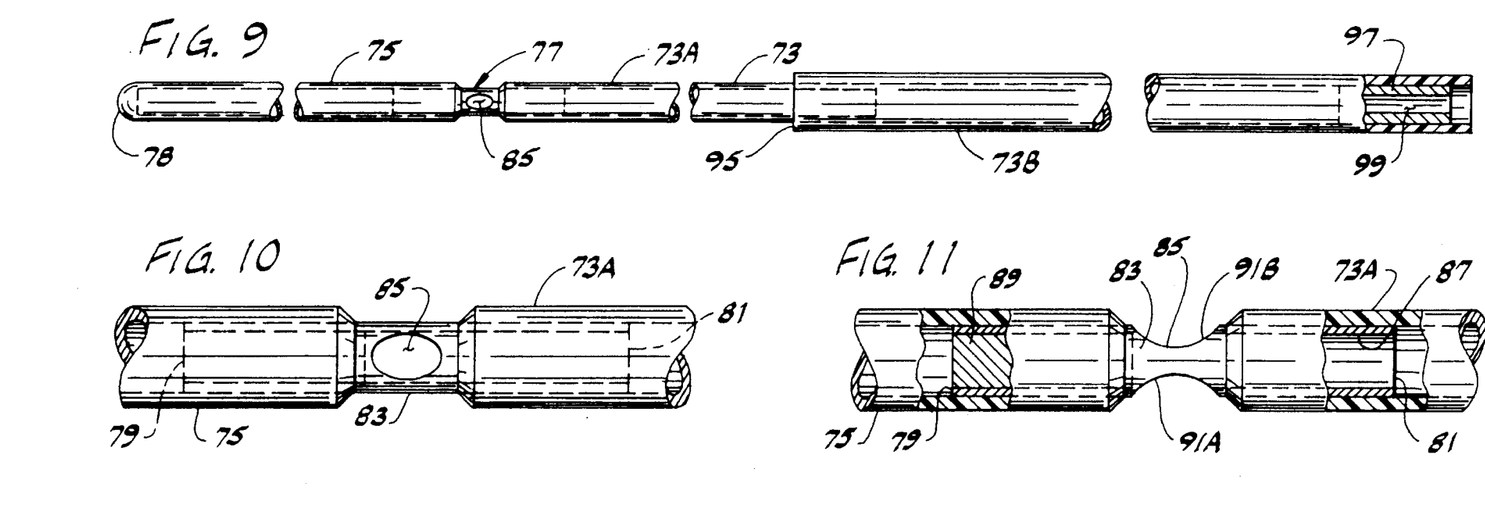
FIG. 9 is a view of an embryo carrier of the system.
FIG. 10 is an enlarged view of part of the carrier of FIG. 9.
FIG. 11 is a view similar to FIG. 10, portions of the carrier being broken away to illustrate details.

The fourth part of the system, shown in FIGS. 9–11, is an embryo carrier, generally designated 71, comprising a tubular member 73, a long flexible guide member 75 forward of the tubular member, and a ported member generally indicated at 77 connecting the tubular member 73 and the guide member 75 in axial alignment. By way of example, the guide member 75 may be formed from a 3.0-in. length of plastic leader tubing having a closed polished forward end 78, an OD of 0.06 in. and an ID of 0.035 in. As shown in FIG. 10, the ported member 77 has a forward end part 79 sealingly press fitted in the rearward end of the guide member 75, a rearward end part 81 sealingly press fitted in the open forward end of the tubular member 73, and a center part 83 having a port 85 therein. This port is disposed between the spaced apart ends of the guide member 75 and the tubular member 73 so that it is exposed.

The forward end 79 part of the ported member 77 is closed to block any flow of fluid therethrough, and the rearward end 81 part of the ported member has a passage 87 which communicates with the aforesaid port 85. By way of example, the ported member 77 may be formed by a length of stainless steel hypodermic tubing (20-gauge, thin wall), and a stainless steel stopper 89 plugging the forward end part 79 of the member. Opposing portions of the side wall of the tubing are removed as shown in FIGS. 10 and 11 to form opposing apertures 91A, 91B in the tubing. These apertures combine to form the aforementioned port 85. As will be described later, the port functions as an inlet through which embryos can enter the carrier 71 and as an outlet through which the embryos can exit into the uterus.

The tubular member 73 may be fabricated from two lengths of tubing, the first being indicated at 73A and the other at 73B. The first piece is of smaller diameter than the second piece and is press fitted into the second piece to form a single tube having a shoulder 95 constituting an external stop at the intersection of the two pieces. By way of example, piece 73A may be a length of semi-flexible plastic tubing having an OD of 0.06 in., an ID of 0.04 in. and a length of 4.0 in., and piece 73B may be a length of hard plastic tubing having an OD of 0.083 in., an ID of 0.0625 in., and a length of 5.25 in. The connection between the two pieces of tubing should be a sealing connection.

A plug 97 of absorbent expandable material (e.g., cotton) is received in the rearward end of the tubular member. This plug is initially annular in shape with a passage 99 through it to permit aspiration of embryos into the carrier by means of an aspirator connected to the rearward end of the tubular member 73B. During such aspiration, this plug 97 expands to close and seal the rearward end of the tubular member, as will be explained later.

The fifth and final part of the system comprises a two-part sheath, generally designated 101, protecting and sealing the embryo carrier 71. The sheath comprises front and back parts designated 103 and 105, respectively, both of which are formed from tubes of plastic, for example, the front end of the front part being closed by a permanent plug 107 and the back end of the back part 105 being open. The back end of the front part is recessed and chamfered as indicated at 109 for receiving the front end of the front part 105 to form a press-fit, sealing connection between the two sheath parts. The front tubular part 103 of the sheath should have a length and inside diameter sufficient to house the guide member 75 and ported member 77 of the carrier, and the back tubular part 105 of the sheath should have a length and inside diameter sufficient to house the tubular member 73 of the carrier.

The use of the system described above and the method of this invention are described below.

The first step in the method of this invention is to sterilize all parts of the system to reduce the risk of contamination during the embryo transfer. Following sterilization, the gripping instrument 21, probe 41 and bar 61 should be preassembled and packed into a plastic bag to avoid contamination. As previously described, this is achieved by inserting the probe, rearward end first, into the forward end of the gripping instrument, and by inserting the bar, forward end first, into the rearward end of the probe.

Figure 12:
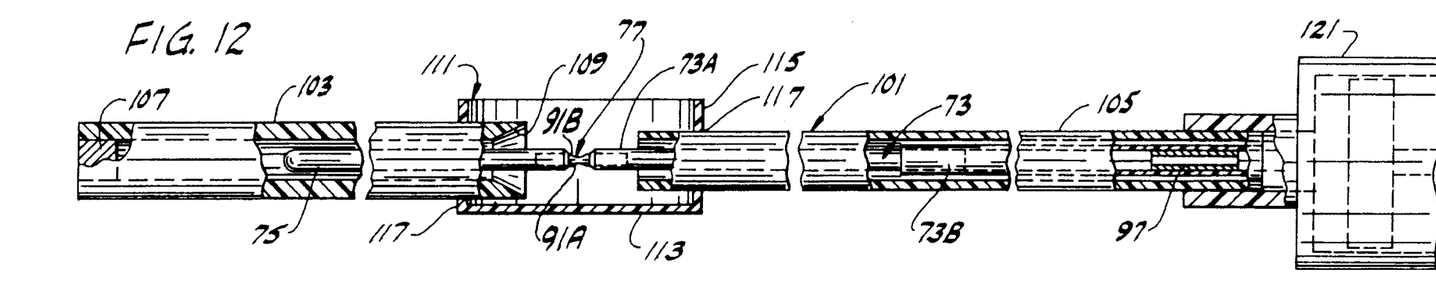
FIGS. 12–15 are views illustration how embryos are loaded into the carrier.
Figures 13, 14, 15:
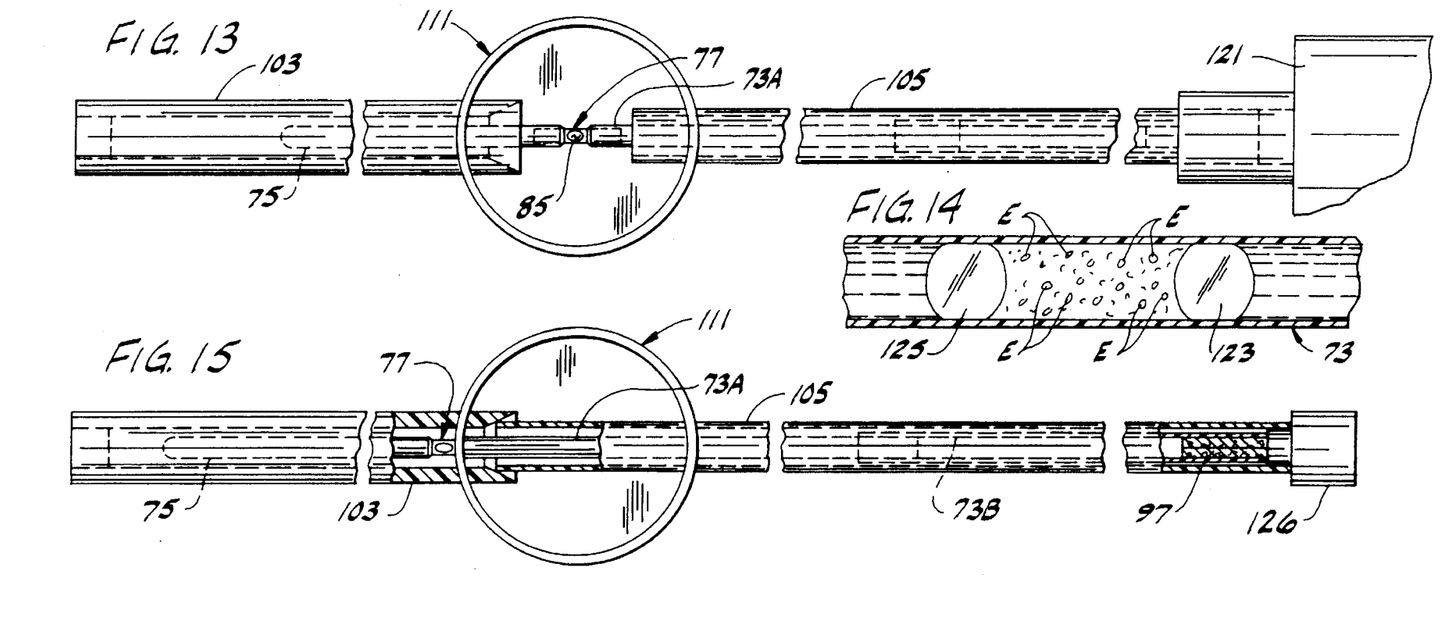

Step two is to load the embryos into the carrier 71. The preferred methodology, illustrated in FIGS. 12–15, involves submerging the port member 77 of the carrier in a suitable fluid culture medium (e.g., TL-Hepes) held in a cup-like receptacle or dish 111 having a bottom 113 and a circular side wall 115 extending up from the bottom. This can be accomplished by first inserting the two-part sheath 101, with the carrier 71 inside, through aligned openings 117 in the side wall 115 of the dish, the fit of the sheath in these openings being sufficiently tight to form a seal. Culture medium suitable for the embryos to be transferred is then deposited in the dish, and the two parts of the sheath are separated to expose the apertures 91A, 91B in the port member 77 (FIGS. 12 and 13).

Using a suitable aspirator, such as a syringe (indicated at 121 in FIG. 12), connected to the open rearward end of the back part 105 of the sheath 101, a predetermined quantity of fluid (e.g., 0.3 ml.) is aspirated into the tubular member 73 of the carrier 71 through the apertures 91A, 91B in the ported member, the apertures thus constituting an inlet of the carrier during this stage of the procedure. No air bubbles should be trapped in the tubular member 73 during this stage of the loading procedure. After the aforesaid predetermined quantity of fluid has been aspirated, the ported member 77 is raised above the fluid in the dish 111 to aspirate a first air bubble 123 into the tubular member 73 (FIG. 14), following which the ported member 77 is resubmerged in the medium. Embryos E are then introduced into the medium by means of a pipette, for example, at a location immediately adjacent the carrier inlet 85, so that they are aspirated along with the medium into the tubular member 73 of the carrier 71. After the embryos have entered the carrier, a second air bubble 125 is aspirated into the carrier so that the embryos are trapped between the two air bubbles (FIG. 14). Following this process, an additional quantity of fluid (e.g., 0.1 ml.) is aspirated into the carrier. This quantity should be sufficient to fill the tubular member 73 to a point where liquid comes into contact with the absorbent plug 97 at the rearward end of the tubular member. Upon absorption of this liquid, the plug expands to close the passage 99 through it, thereby sealing the rearward end of the carrier. The aspirator can then be disconnected and a stopper 123 inserted in the back part 105 of the sheath 101.

After the aspiration is complete, the two parts 103, 105 of the sheath can be pushed together to provide a sealed enclosure for the entire carrier 71 and the embryos E in it. At this point, the sheathed carrier can be transported to the site where the embryo transfer is to take place. The sheath 101 serves two functions, namely, to prevent evaporation of the culture medium carrying the embryos, and to maintain the sterility of the carrier prior to transfer of the embryos into the recipient animal. It should be noted in this regard, that the aforementioned procedures, during which the embryos were loaded into the carrier, should be carried out under sterile conditions.

The next step in the process is to anaesthetize the recipient animal prior to beginning the actual embryo transfer process. Preferably, the animal should be fully anaesthetized prior to the start of this process.

After anaesthetization, lubricant (e.g., a water-based non-toxic lubricant) is applied to the vagina of the recipient animal, and also to the gripping instrument 21, probe 41 and bar 61. With the probe and bar fully retracted inside the gripping instrument to minimize the risk of contamination, the instrument 21 is inserted, screw head 25 first, into the vagina of the animal. This should be done by pushing the instrument forward while rotating the instrument in a counterclockwise direction. This will cause the instrument to advance into the cervix 7 of the animal and to obtain a firm grip or lock on the walls of the cervix, which as mentioned previously, are formed with rounded interdigitated prominences 13.

Figures 16, 17:
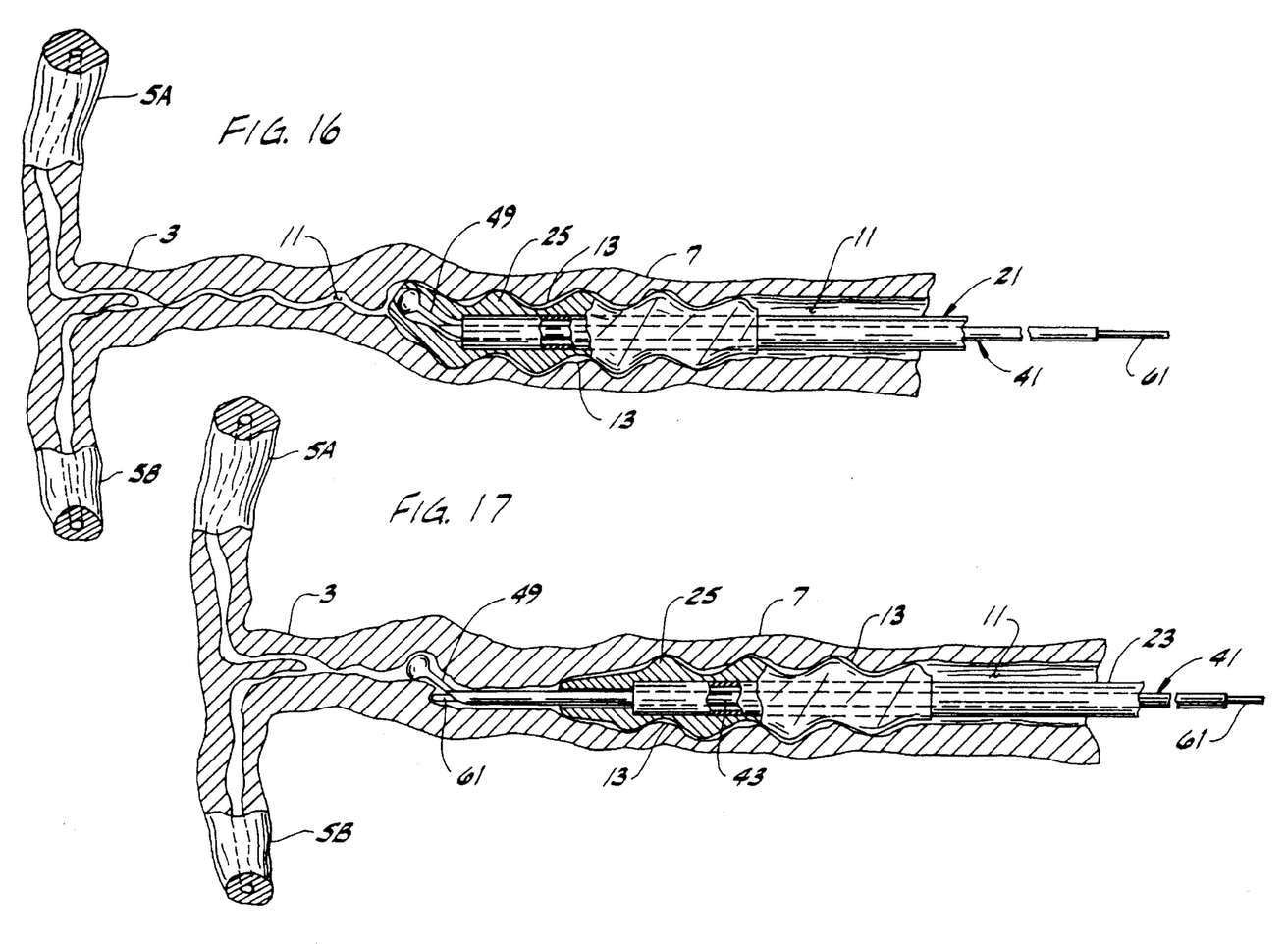
FIGS. 16–20 are views illustrating how the embryos are transferred to the uterus of a pig.
Figure 18:
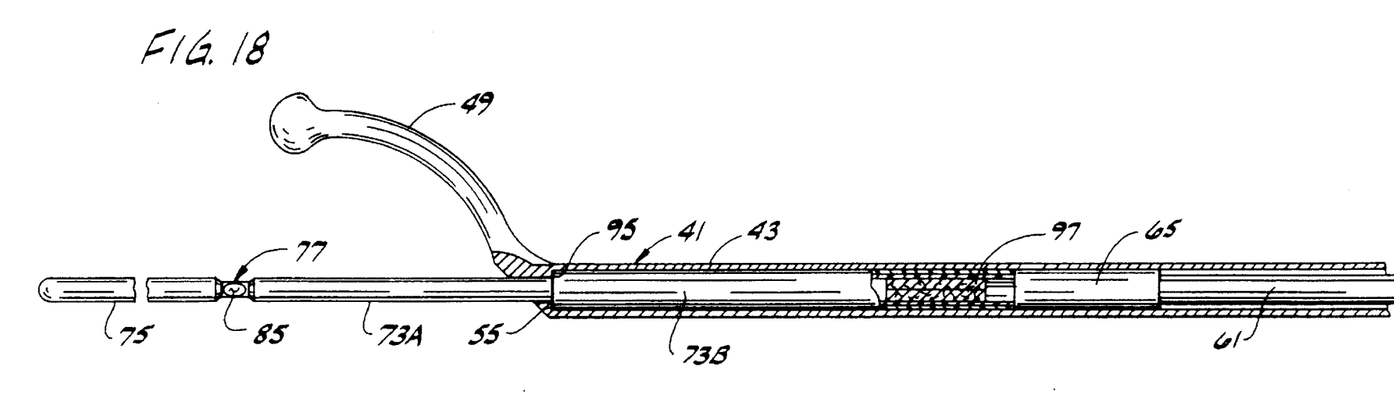

When a firm cervix lock has been established, the gripping instrument 21 is pulled rearwardly to tension and thus straighten the convoluted configuration of the cervix (see FIG. 16). The probe 41 should then be pushed forward very gently beyond the forward end of the gripping instrument to a point where there is significant resistance to further movement (FIG. 17). Encountering such resistance means either that the probe is still positioned inside the cervix or that it has been moved through the cervix and is against the forward end of the body of the uterus. To determine which, the testing bar 61 inside the probe 41 should be pushed forward very gently until a significant resistance is felt, after which the probe should be pulled rearwardly a predetermined distance (e.g., approximately one inch) in relation to the gripping instrument. If the bar 61 can move freely back and forth relative to the probe 41 within a predetermined range of movement (e.g., between marks M1 and M2 on the bar relative to the rearward end of the probe), then the forward end of the probe is likely through the cervix and positioned inside the body 3 of the uterus. Otherwise, the probe is still in the cervix. In the latter situation, the probe 41 should be manipulated to turn the probing finger 49 while pushing the bar 61 gently forward, and while pulling the gripping instrument 21 rearwardly. The combination of these actions tends to work and maneuver the probe through and past the occluding protrubernances in the cervix. This process is carried out until the finger 49 of the probe is through the cervix and positioned in the body of the uterus, as determined by using the bar 61 in the manner described above.

Figures 19, 21:
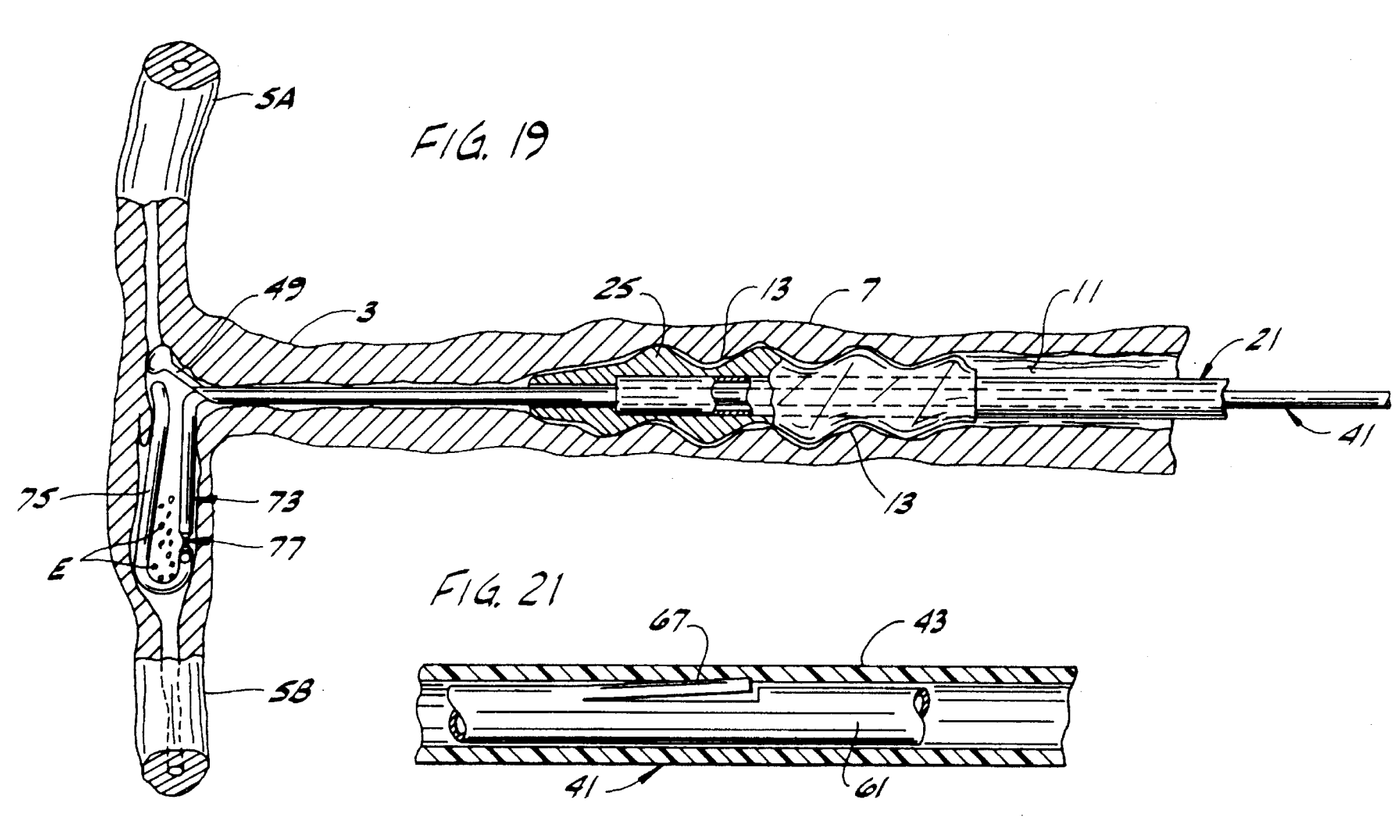
FIG. 21 is a view illustrating how the carrier is removed from the uterus after the embryos have been transferred.

After the forward end 45 of the probe is positioned in or generally adjacent the body 3 of the uterus, the carrier 71 is removed from its sheath 101 and inserted, guide end first, into the open rearward end of the probe 41 (the testing bar 61 having first been removed). The bar 61 is then inserted, pusher end first, into the probe 41 and used to push the carrier forward to a point where the external stop 95 on the carrier engages the internal abutment 55 at the forward end of the probe. This point can be visually confirmed by the use of a score line M4 or the like (see FIG. 7). (When the bar 61 is pushed to a point where score line M4 is at the rearward end of the probe body 43, the stop 95 is in engagement with the abutment 55.) As the carrier moves forward, the long flexible guide member 75 guides the carrier into the lumen of one of the horns 5A, 5B of the uterus to position the ported member 77 of the carrier for release of the embryos E inside the horn, which is the preferred location of release. As illustrated in FIG. 19, the flexible guide member 75 typically forms a loop in the horn of the uterus, which eliminates the possibility of penetrating the highly proliferated lumen epithelial membrane.

Insertion of the carrier into the horn of the uterus should not meet substantial resistance. Substantial resistance indicates that the probe 41 is still in the cervix, not in the body of the uterus. If substantial resistance is encountered, the carrier should be removed and the process described above should be repeated to move the probe to a position where it is in the uterus.

Figure 20:
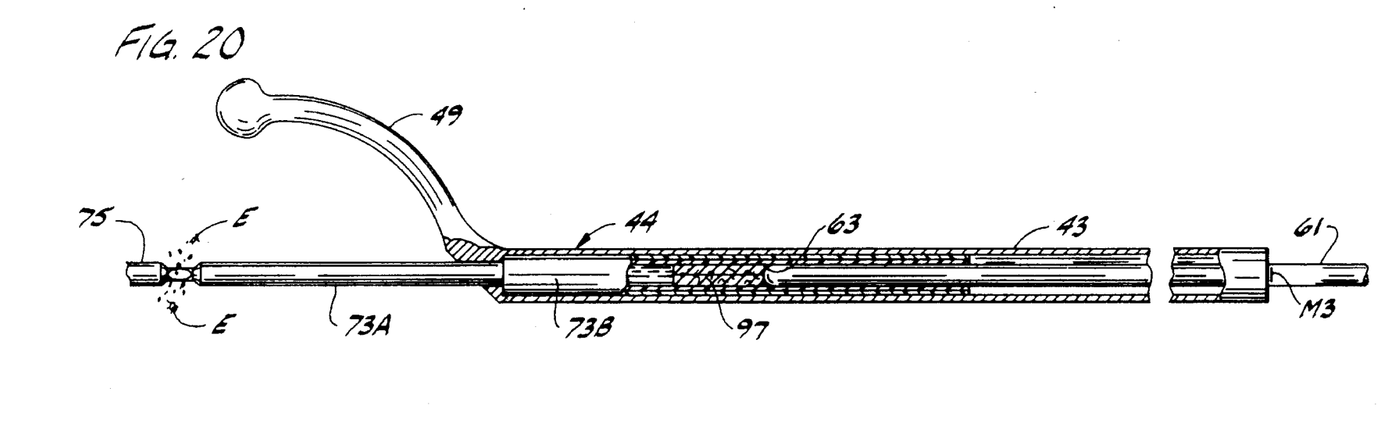

After the carrier 71 is positioned in the horn, the bar 61 is removed from the probe 41, reversed again, and reinserted, forward end first, into the probe. The forward end 78 of the bar 61 has an outside diameter less than the inside diameter of the rearward piece 73B of the tubular member 73 of the carrier, the arrangement being such that the front end of the bar is adapted to enter the tubular member 73 and to push the closed plug 97 forward in the tubular member to a point where the mark M3 on the bar generally aligns with the rearward end of the probe (see FIG. 20). This serves to eject a predetermined amount of fluid (e.g., 0.3 ml.), including the medium containing the embryos, through the outlet 85 of the carrier and into the horn of the uterus. During this process, the carrier is held against forward movement by the abutment of stop 95 against the internal shoulder 55 on the probe. The ejection of the embryos should be effected slowly. The presence of the air bubbles 123, 125 on opposite sides of the slug of medium carrying the embryos ensures that the embryos do not adhere to the walls of the carrier during the ejection process. The total amount of liquid ejected into the uterus during this process is less than 10 ml., preferably less than 1.0 ml., and most preferably about 0.3 ml.

After the embryos are transferred, the bar 61 is pulled rearwardly, which cause the tip of the tongue 67 formed on the bar to bite into or otherwise catch the tubular member 73 of the carrier (FIG. 21). Consequently, movement of the bar 61 in a rearward direction also pulls the carrier 71 in the same direction to remove the carrier from the uterus. The bar and carrier should be retracted to a position in which the carrier is completely inside the probe 41. The probe should then be pulled slowly rearwardly while rotating it gently in a clockwise direction to a point where the probing member 49 is adjacent or fully retracted inside the head 25 of the gripping instrument 21. Following this, the gripping instrument may be turned clockwise to remove all parts out of the vagina. The carrier 71 is then discarded; the gripping instrument, probe and bar are reusable after sterilization. Alternatively, the carrier may also be reusable.

To minimize irritation and to avoid injury during this transfer process, the probe and bar should be manipulated very gently. They should never be forced through substantial resistance.

The system and methodology of this invention have been successfully employed. Embryos (from the 4-cell stage to the blastocyst stage) have been surgically collected from either naturally cycling or superovulated donor pigs on day 5 after estrus via and cultured in TL-Hepes up to 5 hours before the non-surgical embryo transfer. The recipients were either naturally cycling or superovulated gilts on day 4 or 5 after onset of estrus, and had from two to five post-pubertal estrous periods. All of the experimental females were checked for estrus daily by exposing them to a mature boar. Five recipients became pregnant out of a total of sixteen nonsurgical embryo transfers (31.25%). Four recipients farrowed and their litter sizes were 5,9, 3 and 10, respectively, with an average of 6.8±3.3 pigs per litter.

The success of the system and methodology described above are believed to be due to several factors. First, the system and method ensure that the embryos will be released not in the cervix, but rather in the body of the uterus, preferably in the lumen of one uterine horn where they will have the best chance of successful gestation. Successful penetration through the cervical canal, and sensing when this occurs, is made possible by the unique probe 41 of this invention, particularly when used in combination with the testing or detecting bar 61. Second, the embryos are introduced in the uterus with only a minimum of accompanying fluid (most preferably only about 0.3 ml.), so that the uterine environment is not significantly altered from its natural state, which is most suitable for gestation. And third, the process minimizes the risk of trauma, contamination and injury to the animal.

It is contemplated that the present invention may be applicable to animals other than pigs. For example, it is believed the system and methodology described above is suitable for transferring embryos to any female animal having a cervix structure which poses a natural barrier against the conveyance of embryos therethrough. Certain breeds of cattle (e.g., Brahman) fall within this category, for example.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of effecting the non-surgical transplant of embryos into the uterus of an animal, said method involving the use of a long tubular gripping instrument having an open forward end and an external gripping formation generally adjacent its forward end, and a probe extending axially inside the tubular gripping instrument, said probe having a long tubular body with an open forward end and a probing member projecting in a generally non-axial direction from the probe body generally adjacent its forward end, said method comprising the steps of inserting the gripping instrument, forward end first, into a cervix of the uterus of said animal, establishing a grip between walls of the cervix and the external gripping formation on the gripping instrument, while maintaining said grip, pulling the gripping instrument in a rearward direction to straighten the cervix, and simultaneously pushing the probe in a forward direction to advance the probing member beyond the open forward end of the gripping instrument and through the cervix to a position in the body of the uterus, and placing an embryo carrier containing embryos inside the probe body and moving the carrier forwardly through the probe body out the open forward end of the probe body to an embryo release position for release of embryos from the carrier into the uterus.

2. A method as set forth in claim 1 further comprising carrying out a procedure to determine whether the probing member is through the cervix.

3. A method as set forth in claim 2 wherein said procedure comprises advancing the probing member to point where there is significant resistance to further movement, inserting a bar into the probe and pushing in it a forward direction until significant resistance is met, pulling the probing member in a rearward direction a predetermined distance, and moving the probe back and forth to determine the amount of resistance to such movement, the probing member likely being through the uterus if the amount of said resistance is small.

4. A method as set forth in claim 1 wherein the embryo carrier containing embryos is moved to said embryo release position by using a device to push the carrier in a forward direction through the probe body to a position in which an outlet of the carrier is beyond the forward end of the probe body and forward of the probing member, and then forcing the embryos through the outlet into the uterus.

5. A method as set forth in claim 4 wherein said embryo release position is in a horn of the uterus.

6. A method as set forth in claim 4 further comprising pulling the device in a rearward direction after the embryos have been released, said device catching the carrier as the device is pulled rearwardly to move the carrier in a rearward dirction thereby to effect removal of the carrier from the uterus.

7. A method as set forth in claim 1 wherein said embryo carrier has an inlet through which embryos may be loaded into the carrier, and wherein said method further comprises placing said inlet in a liquid medium containing embryos, and aspirating liquid medium containing the embryos into the carrier through said inlet.

8. A method as set forth in claim 7 wherein the amount of liquid medium aspirated into the carrier is less than 1 milliliter.

9. A method as set forth in claim 7 wherein said carrier comprises a tubular member having an open forward end communicating with said inlet, and a rearward end adapted to communicate with an aspirator for aspirating said liquid medium and embryos into the tubular member through said inlet.

10. A method as set forth in claim 9 further comprising aspirating a first air bubble into the tubular member, followed by aspirating liquid medium carrying said embryos into the tubular member, followed by aspirating a second air bubble into the tubular member, so that said liquid medium carrying said embryos is trapped between said air bubbles.

11. A method as set forth in claim 10 further comprising sealing the rearward end of the tubular member after the second air bubble has been aspirated into the tubular member.

12. A method as set forth in claim 9 further comprising enclosing the carrier in a protective sheath after it has been loaded with embryos, and removing the sheath prior to insertion of the carrier into the probe.

13. A method as set forth in claim 1 wherein said gripping formation on the gripping instrument is a screw formation, and said gripping instrument is moved forward in the cervix by exerting a forward force on the instrument while rotating the instrument on a longitudinal axis of the instrument.

14. A method as set forth in claim 1 further comprising maintaining the probing member of the probe inside the gripping instrument until the forward end of the gripping instrument is located in the cervix of the animal.

15. A method for effecting the nonsurgical transplant of embryos into the uterus of an animal, said uterus having a cervix leading to a uterus body, said method comprising the steps of inserting a long tubular gripping instrument in a forward direction with respect to the animal into the cervix to obtain a grip on the walls of the cervix, pulling the gripping instrument rearward direction with respect to the animal; rearwardly to tension the cervix, while pulling the gripping instrument rearwardly inserting a long tubular probe into and through the gripping instrument to a point where a forward end of the probe is generally adjacent the body of the uterus, inserting an embryo carrier containing embryos into the probe and moving it forwardly through the forward end of the probe to an embryo release position in the uterus, and releasing embryos from the embryo carrier into the uterus.

16. A method as set forth in claim 15 further comprising loading a liquid medium carrying embryos into the said embryo carrier.

17. A method as set forth in claim 16 wherein the amount of liquid medium loaded into the embryo carrier is less than one milliliter.

18. A method as set forth in claim 15 wherein a long flexible guide member on the carrier guides the carrier toward a horn of the uterus as the embryo carrier is moved forwardly through the tubular device.

19. A method as set forth in claim 18 further comprising causing the long flexible guide member to loop into a horn of the uterus to position an outlet of the embryo carrier for release of the embryos into the horn.

* * * * *

UNITED STATES PATENT AND TRADEMARK OFFICE
CERTIFICATE OF CORRECTION

PATENT NO. : 5,558,636
DATED : September 24, 1996
INVENTOR(S) : Jiewen Lit et al.

It is certified that error appears in the above-indentified patent and that said Letters Patent is hereby corrected as shown below:

Column 10, claim 15, lines 38-39, "instrument rearward direction with respect to the animal; rearwardly to tension" should read ---instrument in a rearward direction with respect to the animal to tension---.

Signed and Sealed this

Twenty-ninth Day of April, 1997

Attest:

BRUCE LEHMAN

*Attesting Officer*  *Commissioner of Patents and Trademarks*